United States Patent [19]
Mortensen et al.

[11] Patent Number: 5,296,369
[45] Date of Patent: Mar. 22, 1994

[54] **METHOD AND COMPOSITIONS FOR CONTROLLING ROUND-LEAVED MALLOW USING *COLLETOTRICHUM GLOEOSPORIOIDES* F. SP. *MALVAE*, A.T.C.C. 20767**

[75] Inventors: Knud Mortensen, Balgonie; Roberte M. D. Makowski, Regina; James E. Cunningham, Saskatoon; Robert D. Carmichael, Edmonton, all of Canada

[73] Assignees: Her Majesty the Queen in right of Canada, as represented by the Minister of Agriculture, Ontario; Philom Bios, Saskatchewan, both of Canada

[21] Appl. No.: 699,253

[22] Filed: May 13, 1991

Related U.S. Application Data

[63] Continuation-in-part of Ser. No. 174,387, Mar. 28, 1988, abandoned, which is a continuation-in-part of Ser. No. 776,209, Sep. 16, 1985, abandoned.

[51] Int. Cl.$^5$ .................... A01N 63/00; C12N 3/00; C12N 1/14
[52] U.S. Cl. .................... 435/242; 435/261; 435/813; 435/911; 435/254.1; 504/117
[58] Field of Search .............. 435/911, 242, 254, 261, 435/813; 71/79

[56] References Cited

U.S. PATENT DOCUMENTS

| | | | |
|---|---|---|---|
| 3,849,104 | 11/1974 | Daniel et al. | 71/79 |
| 3,999,973 | 12/1976 | Templeton | 71/79 |
| 4,419,120 | 12/1983 | Walker | 71/79 |

FOREIGN PATENT DOCUMENTS 0218386  4/1987  European Pat. Off. .

OTHER PUBLICATIONS

Grant et al., Herbicide Interact. w/ C. gloesporioides f. sp. malvae, . . . and Effect of Selected Pest. on Survival of . . . , (pp. 716–723) (pp. 701–715) 1990.

TeBeest; 1985, Techniques for Testing & Eval. Plant Pathogens for Weed Control, (pp. 123–129).
Kirkpatrick et al., Potential of Colletotrichum malvarum for Biological Control of *Prickly Sida*, 1982, (pp. 323–325).
Stanbury et al., *Principles of Fermentation Technology;* 1984; (pp. 113–116).

*Primary Examiner*—Douglas W. Robinson
*Assistant Examiner*—Deborah K. Ware
*Attorney, Agent, or Firm*—Wegner, Cantor, Mueller & Player

[57] ABSTRACT

Commercial mycoherbicide compositions for the control of round-leaved mallow weeds (*Malva pusilla* Sm.), the active ingredient being the spores of the fungus *Colletotrichum gloeosporioides* f.sp. malvae, ATCC 20767, these spores having been produced by a two-phase multi-staged liquid fermentation process, then separated from the mycelial biomass and concentrated into a spore slurry. The active ingredient of the mycoherbicide compositions, i.e., spores, can be packaged as a concentrated spore slurry or alternatively, dried and then packaged. Both the liquid and dry forms of the myco-herbicide are packaged in gas- and water-impermeable containers. The spores are stabilized prior to packaging or drying by the addition of a stabilizing agent or alternatively, stabilized after drying by adjusting their final water content. The initial, i.e., primary, fermentation phase may be made up of multiple stages and is performed under conditions which are optimized for production of mycelial biomass while restricting spore production. The final-phase fermentation is performed under conditions which limit mycelial biomass production but are optimized for production of the active ingredient, i.e spores. These mycoherbicide compositions are applied by suspending the spore slurries in water or alternatively, suspending the dried spores in water, and followed by spraying of the resulting suspension onto round-leaved mallow weeds. The active ingredient of these mycoherbicidal compositions, i.e., fungal spores, will control only round-leaved mallow weeds, and does not affect other weed species or non-target crop plants.

13 Claims, No Drawings

METHOD AND COMPOSITIONS FOR CONTROLLING ROUND-LEAVED MALLOW USING *COLLETOTRICHUM GLOEOSPORIOIDES* F. SP. *MALVAE*, A.T.C.C. 20767

BACKGROUND OF THE INVENTION

This invention relates to biological control of weeds, particularly round-leaved mallow (*Malva pusilla* Sm.). It is a continuation-in-part of U.S. application Ser. No. 07/174,387 filed Mar. 28, 1988, now abandoned, and which is a continuation-in-part of U.S. application Ser. No. 776,209, filed Sep. 16, 1985, now abandoned.

Endemic pathogens have been used for biological control of weeds. For instance, Daniel et al., U.S. Pat. No. 3,849,104, describes a method for controlling northern jointvetch by inoculation with a species of the fungus Colletotrichum. Templeton, U.S. Pat. No. 3,999,973, shows that *Colletotrichum malvarum* is capable of controlling prickly sida, velvetleaf and non-cultivated mallow species. Walker, U.S. Pat. No. 4,419,120 discusses the use of *Fusarium lateritium* to control prickly sida, velvetleaf and spurred anoda. In Anderson et al., U.S. Pat. No. 4,715,881, there is a discussion of the use of *Colletotrichum coccodes* for the control of eastern black nightshade and related species. Walker, U.S. Pat. No. 4,390,360, shows that *Alternaria cassiae* provides effective control of sicklepod, showy crotalaria and coffee senna.

It has also been taught in U.S. Pat. No. 4,419,120 that a commercially useful fungal pathogen must control two or more important weed species. U.S. Pat. Nos. 4,419,120 and 4,715,881 teach that mycoherbicidal compositions do not require immediate contact with the target plant for infection and control to occur.

Walker, U.S. Pat. No. 4,419,120, and Tabachnik, U.S. Pat. No. 4,837,155, teach that processes disclosed previously for the production of fungal propagules are laboratory processes and do not produce sufficient amounts of material in large-enough volumes in short-enough time periods to be commercially viable. Furthermore, Walker, U.S. Pat. No. 4,419,120, and Tabachnik, U.S. Pat. No. 4,837,155, teach individually and separately, that economic large-scale production of fungal propagules is based on single-phase liquid fermentation processes which may, but not necessarily, consist of multiple stages.

Fungal propagules produced by the previously disclosed processes tend to be very unstable and have very short shelf lives. Consequently, the fungal propagules disclosed in the prior art have not been commercially acceptable.

It is most important for commercial products that they have shelf lives in the order of months, preferably six months or more, at room temperature.

It has also been found with production processes disclosed in the prior art that total spore yields were too low to be cost effective for large scale commercial production (Anderson and Walker, U.S. Pat. No. 4,715,881).

It is also desirable, contrary to what has been stated in the prior art, that commercially useful fungal pathogens be highly selective to a single important weed species. This has the very important advantage of making possible treatment of an actively growing crop to eliminate a troublesome weed without any damage to the crop itself.

Round-leaved mallow has become a troublesome weed in field crops in Western Canada and U.S.A. There are no adequate methods or products to effectively control round-leaved mallow, and it has often been necessary to plow infested fields under.

It is an objective of the present invention to produce commercially viable mycoherbicides, particularly for the treatment of round-leaved mallow.

SUMMARY OF THE INVENTION

According to this invention, it has been found that a newly-isolated species of the fungus Colletotrichum is uniquely-capable of controlling round-leaved mallow weeds (*Malva pusilla* Sm.). The effective species is *Colletotrichum gloeosporioides* f.sp. malvae. ATCC No. 20767.

*Colletotrichum gloeosporioides* f.sp. malvae, referred to hereinafter as "Cgm", has been found to be uniquely-specific in its pathogenicity to round-leaved mallow, while having little or no effect at all on other weed species or non-target crop plants.

Of particular commercial interest is the efficacy of Cgm spores when used as the active ingredient of mycoherbicide compositions. These spores have an excellent shelf life of six months or more when properly produced, processed and stabilized prior to packaging and storage.

Thus, one embodiment of this invention is a method for controlling the weed species, round-leaved mallow (*Malva pusilla* Sm.), which comprises adding to the surfaces of the weed, a commercial mycoherbicidal composition of the fungus *Colletotrichum gloeosporioides* f.sp. malvae, ATCC No. 20767, in sufficient quantity to infect and kill the weed.

This invention also relates to a commercial mycoherbicide composition for the control of round-leaved mallow weeds, which is comprised of the spores of *Collectotrichum gloeosporioides* f.sp. malvae, ATCC No. 20767, as the active ingredient, and a carrier therefor. The active ingredient of the mycoherbicidal composition, i.e. Cgm spores, is stable at ambient temperatures because the spores are stabilized with a stabilizing agent prior to packaging or drying or alternatively, by adjusting their relative humidity after drying.

This invention also relates to a commercial mycoherbicide composition for the control of round-leaved mallow weeds, which is comprised of the spores of *Collectotrichum gloeosporioides* f.sp. malvae, ATCC No. 20767, as the active ingredient in the form of a concentrated spore slurry, and a carrier therefor. The active ingredient of the mycoherbicidal compositions, i.e. Cgm spores, is stable because the spores are stabilized with a stabilizing agent prior to packaging.

This invention also relates to a commercial mycoherbicide composition for the control of round-leaved mallow weeds, which is comprised of the spores of *Colletotrichum gloeosporioides* 30 f.sp. malvae, ATCC No. 20767, as the active ingredient in the form of dried spores, and a carrier therefor. The active ingredient of the mycoherbicidal composition, i.e. Cgm spores, is stable at ambient temperatures because the spores are stabilized with a stabilizing agent prior to drying or alternatively, by adjusting their relative humidity after drying.

In another embodiment of this invention, an unique process is provided for the commercial production of Cgm spores in high yields. This process comprises preparing an inoculum stock consisting of the fungus *Col-* letotrichum gloeosporioides f.sp. malvae, ATCC No. 20767, and using this stock to inoculate a fermenter containing a nutrient-balanced C:N ratio liquid medium. A fermentation is conducted in this fermenter to produce primarily mycelial biomass. If more biomass is desired, then this culture can be serially-transferred to one or more larger fermenters (i.e., multi-stage primary-phase fermentation). After sufficient mycelial biomass has been generated with the primary-phase medium, the mycelial biomass is transferred to a fermenter containing a final-phase liquid medium which limits further mycelial biomass production but stimulates and optimizes spore production. A further fermentation is conducted in this fermenter to produce the desired spores. Thereafter, the spores are processed into a commercial mycoherbicide composition by separating them from the mycelial biomass in the final-phase medium, and then concentrating the resulting spore suspension into a slurry. At this point, the spores may be stabilized by the addition of a stabilizing agent to the slurry, and then packaged in a sealed gas- and water-impermeable container. Alternatively, the spores may be dried, stabilized before drying with a stabilizing agent or alternatively, after drying by adjusting their final moisture content, and then the dried stabilized spores are packaged in a sealed gas- and water-impermeable container.

The primary-phase fermentation medium is nutrient-balanced, has a low C:N ratio, and contains a medium component which suppresses sporulation. The final-phase fermentation medium has an altered C:N ratio relative to the primary-phase medium, and does not contain the sporulation-suppressing medium component.

The spores produced during final-phase fermentation are preferably separated from the mycelial biomass by screening, straining or sieving. The separated spore suspension is preferably concentrated into a slurry by centrifugation or filtration, for subsequent processing. At this point, the concentrated slurry may be stabilized by the addition of a stabilizing agent, then packaged in a sealed, gas- and water-impermeable container.

Alternatively, the concentrated spore slurry is dried, preferably by tray-drying, freeze-drying or spray-drying. The spores are preferably stabilized prior to drying by the addition of a stabilizing agent to the spore slurry or alternatively, by adjusting the relative humidity of dried spores to a constant, preferably in a range between 12% and 33% moisture content. For optimum stability of the commercial mycoherbicide composition, it is preferable to combine the spores with a stabilizing agent before drying, or to adjust the relative humidity of dried spores to a constant in the range of 12% to 33%.

The mycoherbicidal composition containing concentrated spore slurry, and the composition containing dried, stabilized spores, are preferably stored in sealed gas- and water-impermeable containers. They can be stored in this manner for many months without loss of activity. To use the spores as a mycoherbicide, it is simply a matter of opening a container and mixing the spores with water. No special additives are needed to prepare a sprayable composition which can be sprayed directly onto a round-leaved mallow-infested field. Excellent results in controlling this weed have been obtained with applications at a field rate of about $1 \times 10^{11}$ viable spores/hectare.

It has also been found that these mycoherbicidal compositions containing processed and stabilized Cgm spores, are effective against round-leaved mallow weeds at various stages of their growth cycle including seedlings and mature plants. It has also been found that if the application of these mycoherbicidal compositions is followed by a period of drought, these mycoherbicidal compositions may retain their mycoherbicidal properties until sufficient moisture is present for suppression of round-leaved mallow weeds to commence.

DETAILED DESCRIPTION

The *Collectotrichum gloeosporioides* f.sp. malvae, ATCC No. 20767 was originally isolated from seedling blight occurring on round-leaved mallow (*Malva pousilla* Sm.) grown in a greenhouse. Later the disease, appearing as anthracnose symptoms, was observed on round-leaved mallow plants under natural conditions from several locations in Saskatchewan, Canada. Under natural conditions the disease does not develop into epidemic proportions in stands of round-leaved mallow until later in the growing season. However, under greenhouse conditions round-leaved mallow plants were severely attacked and often totally killed when inoculated with this pathogen.

Isolation of *C. gloeosporioides* was done by plating out sections of diseased plant material (surface disinfected for 1 min, rinsed in sterile water) on potato dextrose agar (PDA). Round-leaved mallow and test plants used in these experiments were grown from seeds in a sandy loam soil mixed (3:1) with sphagnum (peat moss) and grown on greenhouse benches at a temperature of 18°-24° C. with a 14 hour day extended with incandescent and fluorescent light. Seeds used were obtained from Regina Research Station seed stock, from research scientists and from seed supply stores. If not specified, plants were inoculated in the well developed seedling stage (2-4 weeks after planting, depending on the plant species). Spores of *C. gloeosporioides* used for inoculating test plants were produced on potato dextrose agar incubated in an incubator (Conviron, I18L) for 6-8 days at 24° C. with a 12 hour light cycle of fluorescent light (275 microeinstein per m sq. per sec.). Spores (conidia) produced in acervuli on potato dextrose agar were transferred to distilled water by means of a bacterial loop. The spore suspension (concentration determined by counting spores in a haemocytometer) was sprayed on test plants by means of an air brush (Paasche Airbrush (Canada) Ltd., Type H-5) operated with a constant air pressure (30 lb/sq. inch) until runoff. Concentrations of spore suspensions were normally 2-5 million spores/ml. After inoculations, test plants were kept in a mist chamber for three days to assure good infection. The mist chamber was constructed on a greenhouse bench and enclosed with transparent polyethylene, the day/night cycle and temperature range in the mist chamber being similar to that of the greenhouse. Mist was supplied by a cool water mister operating 2 minutes out of every 12, creating enough moisture in the chamber to keep plants wet without run-off. After leaving the mist chamber, inoculated plants were kept on greenhouse benches for 15 to 20 days (under regular inspection) until a final disease rating was done using a scale from 0-9:

0: Totally resistant (immune), no visible symptoms.
1: Few restricted lesions developing, covering less than 2% of plant surfaces.
2: Few restricted lesions developing, covering up to 5% of plant surfaces. Lesions in 1 and 2 are very small (0.5 mm diameter) and do not affect plant development.

3: Restricted lesions developing, covering up to 10% of plant surfaces.
4: Restricted lesions developing, covering up to 15% of plant surfaces. Lesions in 3 and 4 are small (2 mm diameter) and do not cause wilting of plant material outside lesion, thus not affecting plant development seriously.
5: Lesion development girdling smaller branches and leaf petioles, causing wilt of up to 20% of plant material.
6: Lesion development girdling smaller branches and leaf petioles, causing wilt of up to 50% of plant material.
7: Lesion development girdling medium size stem branches, causing wilt of up to 75% of plant material.
8: Lesion development girdling main stem branches, causing wilt of up to 90% of plant material.
9: Lesion development girdling all stem branches, causing wilt of more than 90% of plant material.

In a preliminary test it was found that an 18-24 hour mist period after inoculation, where plants were kept wet without runoff, was required to obtain good infection of C. gloeosporioides on round-leaved mallow. First sign of infection is visible 5–6 days after inoculation. It appears as a dark sunken lesion on stems and leaf petioles. After 2 weeks, the lesions (2–5 mm diameter) turn greyish in the center with an almost black margin. Later lesions often coalesce and sever entire stem or leaf petioles resulting in wilting of the stem above the lesion. In the center of the lesion small pinkish dots are visible. These are the acervuli in which oblong (10× 6 $\mu$m) hyalin conidia are produced readily under moist conditions.

The above procedure proved the viability of Cgm as a pathogen for round-leaved mallow weeds, but represented only a laboratory scale production of the mycoherbicide and testing under controlled greenhouse conditions. Accordingly, the invention was further developed to provide a novel production method for producing the mycoherbicide economically in commercial quantities and to produce a mycoherbicidal composition which could be utilized in a commercially practical manner.

Typical prior art previously-disclosed for large-scale production of fungal propagules, incorporated single-phase liquid fermentation processes which may, but not necessarily, include multiple stages (e.g., Templeton, U.S. Pat. No. 3,999,973; Anderson and Walker, U.S. Pat. No. 4,715,881; Walker, U.S. Pat. No. 4,419,120; Tabachnik, U.S. Pat. No. 4,837,155).

In the commercial process of the present invention, the large-scale production of fungal propagules, i.e., spores, includes a two-phase multi-staged liquid fermentation process. The first phase, i.e., primary phase, may consist of multiple stages to increase the amount of mycelial biomass produced during fermentation process. The mycelial biomass and any spores produced during primary-phase fermentation are not recovered, but are used to inoculate the next fermenter stage. The final phase of production, i.e., final-phase fermentation, is where the spores to be used as the active ingredient of commercial mycoherbicide compositions, are produced and subsequently harvested.

The production process is initiated by using an inoculum spore stock to inoculate agar plates, shake flasks or fermenters as appropriate. Spore stocks are produced on a suitable solid agar medium such as sucrose-yeast extract agar (SYE) or potato dextrose agar (PDA). After sufficient growth and sporulation have occurred, the spores are harvested by flooding the surfaces of the agar medium with sterile distilled water and gently agitating. The resulting spore suspension is quickly removed from the agar medium, suspended in a glycerol solution and either used directly or stored at $-70°$ C. Inoculum stocks may also be produced from Cgm grown on SYE or PDA agar by excising the entire culture which may contain mycelium or mycelium plus spores, and homogenizing the entire culture with liquid medium. This type of inoculum stock, i.e., mycelium stock or mycelium plus spores stock, is used immediately after preparation.

The primary-phase fermentation process is initiated by inoculating a nutrient-balanced low C:N ratio liquid medium with an appropriate inoculum stock. The primary-phase medium contains, but is not restricted to, sucrose (10g/l), yeast extract (5 g.1), mono-potassium phosphate (5 g/1), ammonium sulfate (10 g/1) with the pH adjusted to 6. In this medium, ammonium sulfate serves as the sporulation-suppressing component. This primary-phase medium is referred to hereinafter as SYEPN medium.

The primary-phase fermentation is performed under controlled conditions for temperature, pH, aeration, agitation, backpressure and dissolved oxygen, in order to optimize the production of mycelial biomass. For culture volumes between 10 and 200 liters, the conditions used for temperature are 20°–25° C.; pH between 5.5–6.5; aeration between 0.1–1.0 vvm; agitation between 350–600 rpm; back pressure between 0–0.5 bar. Dissolved oxygen is maintained above 50%.

The primary-phase fermentation proceeds until sufficient mycelial biomass has been generated to inoculate a final-phase fermentation vessel. The time period required for completion of primary-phase fermentation will range between 3 to 10 days, depending on the number of transfers to larger vessels required to generate the preferred volume of mycelial biomass required for transfer into the final-phase fermentation vessel.

After the primary-phase fermentation has been completed, the final-phase fermentation is initiated by inoculation of the final-phase liquid medium with the preferred volume of primary-phase culture. The final-phase medium has an altered C:N ratio relative to the primary phase medium and does not contain a sporulation-suppressing component, such that spore production is optimized. The C:N ratio of the final-phase medium is altered by adjusting the ratio of sucrose:yeast extract:tryptic soy broth. Typically, the final-phase medium contains, but is not restricted to, the following components: sucrose (30 g/l), yeast extract (5 g/l ), mono-potassium phosphate (5 g/l), tryptic soy broth (30 g/l), with the pH adjusted to 6. This final-phase medium is referred to hereinafter as SYEP+TSB medium.

Antibiotic compounds may be added to the media to ensure biological purity of the Cgm culture during the production process. For example Penstrep (Sigma cat. no. P0906) may be added to the primary-phase medium such that the medium contains 50 UI/ml penicillin and 0.05 mg/ml streptomycin.

The final-phase fermentation is performed under controlled conditions for temperature, pH, aeration, agitation, backpressure and dissolved oxygen, in order to optimize the production of spores. For culture volumes between 10 and 5000 liters, the conditions used for temperature are 10°–28° C.; pH between 5.5–6.5; aeration between 0.1–1.0 vvm; agitation between 50–600 rpm;

backpressure between 0–0.5 bar. Dissolved oxygen is maintained above 50%.

The final product of the final-phase fermentation consists of mycelial biomass and spores, and typically occurs within 60 to 72 hours with spore yields in the range of $2 \times 10^7$ to $1 \times 10^8$ spores/ml. The spores are separated from the mycelial biomass by screening, sieving or straining. The resulting spore suspension is concentrated into a slurry by centrifugation or filtration. The concentrated spore slurry is stabilized by the addition of a stabilizing agent, then packaged in a sealed gas- and water-impermeable container. Alternatively, the concentrated spore slurry may be dried, preferably using a process such as tray-drying, freeze-drying or spray-drying.

Storage stability of the active ingredient, i.e., the spores, is greatly improved if the spores are stabilized prior to packaging. Spores may be stabilized prior to packaging or drying by the addition to the concentrated spore slurry, of a stabilizing agent such as, but not restricted to sucrose. Alternatively, dried spores may be stabilized by adjusting their final moisture content to a constant in the range of 12% to 33%. Stabilized spores are preferably packaged in gas- and water-impermeable containers.

Further specific embodiments of this invention are illustrated by the following non-limiting examples.

EXAMPLE 1

*C. gloeosporioides* f.sp. malvae was isolated from diseased round-leaved mallow plants from four different locations in Saskatchewan, Canada, namely Antler, Estuary, Lockwood and Regina. These were prepared and tested in accordance with the procedures described above and the pathogenicity was determined on round-leaved mallow at different growth stages from the young seedling stage (2 weeks old) to fully mature plants (10 to 12 weeks old). The results are shown in Table I below:

TABLE 1

Pathogenicity of *C. gloeosporioides* from four different locations in Saskatchewan on round-leaved mallow at varying plant stages.

| Origin of isolate | Inoculum conc. (mill. spores per ml.) | Age of r.l.m. plants at inoculation (weeks) | | | | | |
|---|---|---|---|---|---|---|---|
| | | 2 | 3 | 7 | 9 | 10 | 12 |
| Antler | 8.5 | 9* | 9 | 9 | 9 | 7 | 7 |
| Estuary | 5.5 | 9 | 9 | 8 | 8 | 7 | 7 |
| Lockwood | 8.5 | 9 | 9 | 9 | 9 | 8 | 7 |
| Regina | 7.6 | 9 | 6 | 6 | 6 | 6 | 6 |

*Disease rating 17 days after inoculation (scale: 0–9).

EXAMPLE 2

Round-leaved mallow seeds collected from four locations in Saskatchewan (Regina, Raymore, Strasbourg and Mossbank), and two locations in Manitoba (Manitou and Steinbach) and common mallow (*Malva neglecta*) from Summerland, B.C. were planted and grown under greenhouse condition and inoculated with the Regina isolate of *C. gloeosporioides*. A.T.C.C. No. 20767.

(a) The round-leaved mallow plants were inoculated twice with 10 days interval (inoculum concentration: 2.8 mill. and 9.9 million spores/ml) and rated 14 days after the last inoculation. The results were:

| Rep. | 1 | 2 | Mean | Total No. of plants tested |
|---|---|---|---|---|
| Regina, Sk. | 8 | 8 | 8 | 5 |
| Raymore, Sk. | 8 | 8 | 8 | 6 |
| Strasbourg, Sk. | 6 | 6 | 6 | 3 |
| Mossbank, Sk. | 8 | 8 | 8 | 9 |
| Manitou, Man. | 9 | 9 | 9 | 5 |
| Steinbach, Man. | 9 | — | 9 | 2 |

(b) The procedure of part (a) was repeated but using an inoculum concentration of 19 million spores/ml and rated 17 days after inoculation. The results were:

| Rep. | 1 | 2 | 3 | Mean* | Total No. of plants tested |
|---|---|---|---|---|---|
| Regina, Sk. | 8 | 8 | 8 | 8 | 4 |
| Raymore, Sk. | 6 | 7 | 4 | 5.7 +− 0.9 | 6 |
| Strasbourg, Sk. | 4 | — | — | 4 | 1 |
| Mossbank, Sk. | 6 | — | — | 6 | 3 |
| Manitou, Man. | 9 | 9 | 9 | 9 | 9 |
| Steinbach, Man. | 9 | 9 | 8 | 8.7 +− 0.3 | 7 |

*Mean +− standard error of mean.

(c) The procedure of part (a) was repeated but using an inoculum concentration of 6.3 million spores/ml and rated 20 days after inoculation. The results were:

| Rep. | 1 | 2 | 3 | 4 | Mean* | Total No. of plants tested |
|---|---|---|---|---|---|---|
| Regina, Sk. | 4 | 8 | 8 | — | 6.7 +− 1.3 | 11 |
| Raymore, Sk. | 8 | 8 | 8 | 7 | 7.8 +− 0.3 | 9 |
| Strasbourg, Sk. | 4 | 6 | 6 | 6 | 5.5 +− 0.5 | 14 |
| Mossbank, Sk. | 5 | 7 | 5 | 5 | 5.5 +− 0.5 | 13 |
| Manitou, Man. | 9 | 4 | 4 | — | 5.7 +− 1.7 | 5 |
| Steinbach, Man. | 8 | 8 | 9 | 7 | 8.0 +− 0.4 | 13 |
| Summerland, B.C.** | 4 | 4 | 4 | 4 | 4.0 +− 0.0 | 15 |

*Mean +− standard of error of mean,
** Common mallow.

EXAMPLE 3

Using the procedures described above, pathogenicity tests were conducted on a range of test plant species inoculated with *C. gloeosporioides*, A.T.C.C. No. 20767. The results were shown in Table 2 below:

TABLE 2

Pathogenicity test of *Colletotrichum gloeosporioides* on selected plant species

| Plant Species tested | No. of plants tested | Disease scale (0–9) |
|---|---|---|
| Malvaceae: | | |
| *Malva pusilla* Sm. (round-leaved mallow) | 18 | 7–9 |
| *M. alcea* L. | 5 | 5 |
| *M. alcea* L. var. f (Cav.) C. Koch Fastigiata | 19 | 7 |
| *M. neglecta* Wallr. (common mallow) | 2 | 7 |
| *M. moschata* L. (musk mallow) | 4 | 4 |
| *M. sylvestris* L. | 1 | 2 |
| *Althaea rosea* Cav. (hollyhock) | | |
| cv. Chater's Double mixed | 6 | 3 |
| cv. Majorette Mixed | 2 | 0 |
| cv. Summer Carnival | 2 | 0 |
| Sidalceae sp. TM Special Hybrid | 1 | 0 |
| *Anoda cristata* Schlecht (spurred anoda) | 28 | 0 |
| *Sida spinosa* L. (prickly sida) | 18 | 0 |
| *Abutilon theophrasti* Medic (velvetleaf) | 10 | 6–7 |
| *Pavonia hastata* Cav. | 3 | 0 |
| *Malope trifida* Cav. | 7 | 4 |
| *Gossypium hirsutum* L. (cotton) | | |
| cv. Pima S-5 | 4 | 0 |
| cv. DPL - 61 | 5 | 0 |

TABLE 2-continued
Pathogenicity test of *Colletotrichum gloeosporioides* on selected plant species

| Plant Species tested | No. of plants tested | Disease scale (0–9) |
|---|---|---|
| cv. Stoneville 213 | 6 | 0 |
| *Lagunaria patersonii* Don. | 1 | 0 |
| *Hibiscus trionum* L. (Venice mallow) | 12 | 4 |
| *H. esculentus* L. (okra) cv. Perkin's Mammoth Longpod | 9 | 0 |
| *H. sabdariffa* L. | 1 | 0 |
| Caryophyllaceae: | | |
| *Saponaria vaccaria* L. (cow cockle) | 21 | 0 |
| *Dianthus caryophyllus* L. (carnation) cv. Gaiety Double Mixed | 21 | 0 |
| Compositae: | | |
| *Helianthus annuus* L. (sunflower) | 11 | 0 |
| *Carthamus tinctorius* L. (safflower) cv. S208 | 5 | 1 |
| *Lactuca sativa* L. (lettuce) cv. Red Salad Bowl | 63 | 0 |
| Leguminoseae: | | |
| *Medicago sativa* L. (alfalfa) cv. Algonquin | 24 | 0 |
| *Lens culinaris* Medic. (lentils) | 12 | 0 |
| *Phaseolus vulgaris* L. cv. Pencil Pod Black Wax | 7 | 0 |
| *Pisium sativum* L. (field peas) cv. Century | 5 | 0 |
| *Vicia faba* L. (fababeans) cv. Herz Freyea | 9 | 0 |
| *Glycine max* (L.) Merrill (soybeans) | | |
| cv. Kentland | 13 | 0 |
| cv. Maple Arrow | 9 | 0 |
| cv. Corsoy 79 | 10 | 0 |
| *Aeschynomene virqinica* (L.) B.S.P. (northern jointvetch) | 6 | 0 |
| Linaceae: | | |
| *Linum usitatissimum* L. (flax) cv. Noralta | 34 | 0 |
| Cruciferae: | | |
| *Brassica napus* L. (rapeseed) cv. Regent | 30 | 0 |
| *B. campestris* L. (rapeseed) cv. Candle | 79 | 0 |
| *B. hirta* Moench (white mustard) | 47 | 1 |
| Solanaceae: | | |
| *Lycopersicon esculentum* Mill. (tomato) cv. Bonny Best | 12 | 0 |
| Chenopodiaceae: | | |
| *Beta vulgaris* L. (sugarbeets) cv. Detroit Dark Red | 28 | 0 |
| Polygonaceae: | | |
| *Fagopyrum esculentum* Moench (buckwheat) | 3 | 0 |
| Umbelliferae: | | |
| *Daucus carota* L. (carrots) cv. Early Cross Hybrid | 36 | 0 |
| Cucurbitaceae: | | |
| *Cucumis sativus* L. (cucumber) cv. Chicago Pickling | 5 | 0 |
| Graminae: | | |
| *Triticum aestivum* L. (wheat) cv. Nepawa | 13 | 0 |
| *Hordeum vulgare* L. (barley) cv. Betzes | 16 | 0 |
| *Avena sativa* L. (oats) cv. Cavell | 13 | 0 |
| *Secale cereale* L. (rye) cv. Frontier | 10 | 0 |
| *Zea mays* L. (corn) cv. Gold Bantam | 3 | 0 |
| *Phalaris canariensis* (canary grass) cv. Keet | 50 | 0 |

*0: no symptoms observed, 9: more than 90 percent of test plants killed.

The above results showed that only species in the Malvaceae family were susceptible except for very small restricted lesion development on cotyledons of safflower (*Carthamus tinctorius*) and white mustard (*Brassica hirta*) which did not harm the plants. Only a few species in the Malva genus plus velvetleaf (*Abutilon theophrasti* Medic.) were susceptible (rated 5 or higher on the 0–9 disease scale). Restricted leaf lesions were observed on *M. moschata, M. sylvestris, Altheae rosea, Malope trifida* and *Hibiscus trionum,* but none of these ornamental plant species were damaged seriously and under greenhouse conditions they outgrew the disease.

All three cultivars of cotton (*Gossypium hirsutum* L.) included in the tests were immune.

EXAMLE 4

Tests were conducted to compare the *C. gloeosporioides*, A.T.C.C. No. 20767, of this invention with two known species of Colletotrichum, *C. gloeosporioides* (sp. aeschynomene and *C. malvarum*).

*C. gloeosporioides* from round-leaved mallow grows well on several agar media. On PDA it produces a white greyish mycelium, which very quickly turns black and pinkish masses of spores are produced readily in acervuli on young mycelium, but to a lesser extent in older cultures. *C. gloeosporioides* f. sp. aeschynomene grew slightly faster on PDA, produced spores abundantly, but did not develop as much dark mycelium. *C. malvarum* was similar to *C. gloeosporioides* from round-leaved mallow on PDA, only acervuli with spores were much smaller. Conidia sizes (means of measurements on 15 spores per fungi) were:

*C. gloeosporioides,* round-leaved mallow 10.8+-0.4 by 6.0+-0.3 μm, range: 8.1-14.1 by 4.0-8.1 μm. *C. gloeosporioides* f. sp. aeschynomene 14.5+-0.3 by 4.7+-0.2 μm, range: 12.1-16.2 by 4.0-6.1 μm. *C. malvarum* 12.4+−0.3 by 5.6+−0.1 μm, range: 10.1-14.1 by 5.1≠6.1 μm.

Thus the three fungi can be distinguished morphologically in cultures on PDA. As shown in Table 2, *C. gloeosporioides,* round-leaved mallow, was not pathogenic on northern jointvetch and prickly sida, the hosts of *C. gloeosporioides* f. sp. aeschynomene and *C. malvarum,* respectively. Both *C. gloeosporioides* f. sp. aeschynomene and *C. malvarum* were non-pathogenic on round-leaved mallow.

According to Daniel et al., "Biological control of northern jointvetch in rice with an endemic fungal disease", Weed Science 21: 303-307 (1973), *C. gloeosporioides* f. sp. aeschynomene was pathogenic only on northern jointvetch and Indian vetch but Malvaceae species tested (cotton, okra) were immune. That indicates that the host range of *C. gloeosporioides* f. sp. aeschynomene and *C. gloeosporioides* from round-leaved mallow does not overlap.

According to Kirkpatrick et. al., "Potential of *Colletotrichum malvarum* for biological control of prickly sida", Plant Disease 66: 323-325, (1982), *C. malvarum* was pathogenic only on prickly sida and *Althaea rosea* (hollyhock) and immune to five other Malvaceae species (*Abutilon theophrasti, Anoda cristata, Gyssypium hirsutum, Hibiscus esculentus* and *H. trionum*). Hollyhock is the only species that showed some susceptibility to both *C. malvarum* and *C. gloeosporioides* from round-leaved mallow.

EXAMPLE 5

The purpose of this experiment was to see if *C. gloeosporioides* A.T.C.C. No. 20767 a) can be cultured on velvetleaf for successive generations and b) its pathogenicity is stable or can a strain more adapted to velvetleaf possibly be selected. Typical lesions of *C. gloeosporioides* (round-leaved mallow) occur as stem lesions, mainly at the base of the stems, but occur quite frequently on upper stem parts also. A few infections observed on leaves, were restricted and did not cause serious harm to the plants.

The original inoculum of *C. gloeosporioides* (round-leaved mallow) for velvetleaf was bulked from several isolations from infected round-leaved mallow plants. This was done to have as much variation in the culture as possible. After incubation of inoculated velvetleaf plants, several isolations were made from developed lesions (3 pots, 10 plants) and spores from these isolations cultured on PDA (*C. gleosporioides* velvetleaf 1st generation) were bulked in a spore suspension (heavy, concentration not determined) and sprayed on 3 pots of new velvet-leaf plants. Isolations were made from lesions on 2 plants per pot, spores from these isolations (*C. gloeosporioides* velvetleaf 2nd generation) were bulked and inoculated on a new set of velvetleaf plants (10 pots, 65 plants). From the 2nd generation lesions isolations were made from several lesions at the base of stems on plants from 2 pots, and from several upper stem lesions on plants from two other pots. Spores from each isolation (base and top lesions) (*C. gloeosporioides* 3rd generation) were bulked and inoculated on a new set of velvetleaf plants (3 pots, 4-10 plants per pot). After each inoculation, isolations from lesions on two plants per pot per culture were made. Spores from all isolations of a culture were bulked in a spore suspension and inoculated on a new set of velvetleaf plants (3 pots of 4-10 plants). This was repeated for 6 more generations of the two cultures (originating from base and top lesions). Along with these inoculations (from the fourth generation on) *C. gloeosporioides* (round-leaved mallow) was inoculated on one pot of round-leaved mallow and a set of velvetleaf plants. *C. gloeosporioides* (round-leaved mallow) spores isolated from the round-leaved mallow plants were then used in the following generation. This was done to have a direct comparison with the cultures cultured on velvetleaf. Seventeen to 20 days after each inoculation a disease rating was done on the inoculated velvetleaf plants in a pot using the 0-9 scale. Results of the above are shown in Table 3. The two cultures (originating from base and top lesions) were similar and, therefore, lumped, thus the data for *C. gloeosporioides* velvet-leaf and *C. gloeosporioides* round-leaved mallow in Table 3 are based on six and three replications, respectively.

TABLE 3

*C. gloeosporioides* (round-leaved mallow) cultured on velvetleaf for 9 generations under greenhouse conditions.

| Number of inoculations (generations) | *C. gloeosporioides* velvetleaf | | *C. gloeosporioides* round-leaved mallow | |
|---|---|---|---|---|
| | No. of plants tested | Disease rating (0-9)* | No. of plants tested | Disease rating (0-9)* |
| 1st generation | 26 | 7.7 (7-8) | — | |
| 2nd generation | 65 | 7.6 (5-9) | — | |
| 3rd generation | 44 | 7.2 (5-9) | — | |
| 4th generation | 42 | 7.3 (5-8) | 19 | 7.0 (6-8) |
| 5th generation | 46 | 7.6 (7-9) | 28 | 7.3 (7-8) |
| 6th generation | 50 | 6.0 (5-7) | 20 | 6.3 (5-7) |
| 7th generation | 45 | 7.0 (6-9) | 33 | 6.3 (6-7) |
| 8th generation | 42 | 7.2 (6-8) | 25 | 7.7 (7-9) |
| 9th generation | 39 | 7.3 (6-8) | 13 | 7.0 (7-7) |

*Average of 3 pots in 1st generation, 10 pots in 2nd generation, 6 pots in 3rd to 9th generations.
**Average of 3 pots.

The results in Table 3 indicate that there were no differences in pathogenicity between cultures on velvetleaf for 9 generations and a culture cultured on round-leaved mallow. A test done at the end of the experiment, where 3 pots (24 plants) of round-leaved mallow were inoculated with *C. gloeosporioides* (round-leaved mallow) and another 3 pots (33 plants) of round-leaved mallow with *C. gloeosporioides* velvetleaf 10th generation, resulted in a disease rating of 6.3 (range: 5-8) and 8.7 (range: 8-9) for *C. gloeosporioides* (round-leaved mallow) and *C. gloeosporioides* (velvetleaf) 10th generation, respectively. This would indicate that the pathogenicity of *C. gloeosporioides* from round-leaved mallow is stable on both of these host plants.

EXAMPLE 6

Using the procedures of Examples 1-3 above, pathogenicity tests were conducted on three mallow test plants by inoculation with *C. gloeosporioides*, ATCC No. 20767. The mallow plants were *M. pusilla* Sm. and *M. neglecta* Wallr. as described hereinbefore and *M. parviflora*, with 30 plants of each species being tested. The results based on a disease scale of 0-9 were:

| Days after Inoculation | 7 | 14 | 21 | 28 |
|---|---|---|---|---|
| *M. neglecta* | 4.3 | 5.7 | 6.3 | 6.7 |
| *M. parviflora* | 6.0 | 8.3 | 9.0 | 9.0 |
| *M. pusilla* | 7.7 | 9.0 | 9.0 | 9.0 |

Commercial Production and Testing

The above Examples 1 to 6 all relate to mycoherbicides produced on a laboratory scale. The testing was also generally conducted under controlled conditions, e.g. greenhouse and/or growth chamber.

In the following Examples, a process is described for commercial production of dried and stabilized spores of Cgm and the results from field trials with this mycoherbicide.

Examples 1 to 6 show that Cgm is effective against three different mallows, *M. neglecta*, *M. parviflora* and *M. pousilla*, as well as velvetleaf. However, subsequent field trials have shown conclusively that under field conditions Cgm is ineffective against velvetleaf as well as *M. neglecta* and *M. parviflora*.

EXAMPLE 7

The following example is of a small-scale, three-stage, two-phase fermentation process for the production of Cgm spores.

(A) Primary-phase fermentation.

A Cgm Production Inoculum Stock Culture was plated onto SYE agar and grown at room temperature for 5 days. Spores produced were suspended in sterile culture medium and transferred into 5 vessels, each containing 150 ml of SYEPN medium (primary-phase medium) and grown under controlled conditions (stage 1). After 3-days' growth in the stage-1 vessels, the stage-1 primary-phase mycelial biomass cultures were pooled and transferred into a vessel containing 16 l of SYEPN medium and grown under controlled conditions (stage 2).

(B) Final-phase fermentation.

After 2-days' growth in the stage-2 vessel, the stage-2 primary-phase mycelial biomass culture was transferred into a vessel containing 170 l of SYEP (final-phase medium) and grown under controlled conditions (stage 3). After a 60-hour fermentation in the stage-3 vessel, the titre of spores produced was $3 \times 10^7$ spores/ml.

(C) Processing

After the 60-hour fermentation in the final-phase medium, the spores produced were separated from the mycelial biomass by sieving. The resulting spore suspension was concentrated by centrifugation. The resulting concentrated spore slurry was tray-dried. The viability of the dried spores was $2.0 \times 10^9$ cfu/g (i.e., colony-forming-units/gram of product). The relative humidity of the dried spores was adjusted to a constant by placing the dried spore product into a sealed chamber containing an atmosphere equilibrated with a saturated LiCl solution. The stabilized spores were packaged in a gas- and water-impermeable container.

EXAMPLE 8

The following example is of a large-scale, four-stage, two-phase fermentation process for production of Cgm spores.

(A) Primary-phase fermentation.

A Cgm Production Inoculum Stock Culture was plated onto SYE agar and grown at room temperature for 6 days. Spores produced were suspended in sterile distilled water and transferred into 5 vessels, each containing 150 ml of SYEPN medium (primary-phase medium) and grown under controlled conditions (stage 1). After 3-days' growth in the stage-1 vessels, the stage-1 primary-phase mycelial biomass cultures were pooled and transferred into a vessel containing 16 1 of SYEPN medium and grown under controlled conditions (stage 2). After 2-days' growth stage-2 vessel, the mycelial biomass was transferred into a vessel containing 170 1 of SYEPN medium and grown under controlled conditions (stage 3).

(B) Final-phase fermentation.

After a 1-day growth period in the stage-3 vessel, the stage-3 primary-phase mycelial biomass culture was transferred into a vessel containing 1000 1 of SYEP+TSB (final-phase medium) and grown under controlling conditions (stage 4). After a 72-hour fermentation in the stage-4 vessel, the titre of spores produced was $2.2 \times 10^7$ spores/ml.

(C) Processing.

After the 72-hour fermentation in the final-phase medium, the spores produced were separated from the mycelial biomass by sieving. The resulting spore suspension was concentrated by centrifugation. The resulting concentrated spore slurry was stabilized by the addition of sucrose, and then tray-dried. The viability of the dried spores was $2.9 \times 10^8$ cfu/g (i.e., colony-forming-units/gram of product). The stabilized spores were packaged in gas- and water-impermeable containers.

EXAMPLE 9

Field trials were conducted to determine the tolerance of non-target crop plants to the Cgm mycoherbicide of this invention. Eight crop species were used in this study, namely sunflower, safflower, sugarbeet, wheat, canola, mustard, flax and lentil. The leaf stage of the plants at the time of application is as follows:
a) Sunflower: three leaf stage
b) Safflower, sugarbeet and wheat: four to five leaf stage
c) Canola and mustard: five leaf stage
d) Flax and lentil: twelve to fifteen cm. in height.

Eight pots of round-leaved mallow plants were also placed in the field plots during spore application to ensure that the inoculum and spray conditions were satisfactory.

The plants were treated with Cgm at $1.2 \times 10^{12}$ viable spores per hectare. Two replicates were used with one set of pots from each replicate being left in the field overnight and the other set placed in a dew chamber in the dark at 20° C. for 24 hours following application.

Both sets of pots were then returned to a growth chamber and monitored for disease development weekly for a three-week period.

At the end of the period, all round-leaved mallow plants which had been subjected to a 24 hour dew period following Cgm spore application were dead.

The Cgm had no adverse effect on crop yield or development on any of the cultivars of canola, flax, lentil, mustard, sugarbeet, sunflower, wheat and two cultivars of safflower, with the Cgm having been applied at 4 times the recommended rate. A third cultivar of safflower was the most susceptible with a significantly lower biomass in the treated than in the untreated plots. Except from safflower, Cgm was recovered from very few plots, only in trace amounts, and only at the two-week isolation.

From these tests, there was no evidence that latent infections would affect non-crop target plants or that cgm would build up in the field.

EXAMPLE 10

The commercial Cgm mycoherbicide of this invention was evaluated in field trials on *Malva parviflora*.

*Malva parviflora* seedlings were grown and planted in 6 ft. $\times$ 6 ft. blocks, with nine *M. parviflora* plants at 2 ft intervals. At the time of treatment, average *M. parviflora* plants were 4 to 5 inches in diameter, with ten to fifteen leaves. Local existing weeds included *M. parviflora*, redstem filaree, Italian ryegrass and annual bluegrass.

The *M. parviflora* plants were first treated with a commercial 2,4-DP herbicide, with the mycoherbicide of the present invention being applied the following day at a 1-acre equivalent of $4.8 \times 10^{11}$ viable spores.

Evaluations were made approximately every two weeks to determine the degree of Cgm infection of the *M. parviflora* plants. Only one plant showed any sign of infection and that was on a single leaf petiole. The leaf blade was still green and normal looking at the time. It was found that the combination of a low concentration of 2,4-DP and the Cgm of this invention had no affect in fungus establishment on the *M. parviflora* plants, while high dosages of 2,4-DP and the Cgm spores severely retarded the plants but did not kill any of them. Thus, the conclusion was that *M. parviflora* is extremely tolerant to the Cgm spores of the present invention.

We claim:
1. A method for commercial-scale production of a fungal product having mycoherbicidal activity against round-leaved mallow (*Malva pusilla* Sm.), said method comprising the steps of
   (a) preparing an inoculum stock of the fungus *Colletotrichum gloeosporioides* f.sp. malvae, ATCC 20767,
   (b) in a multi-stage primary fermentation inoculating a first vessel containing a primary fermentation medium with said inoculum, said primary fermentation medium having a low carbon:nitrogen ratio to maximize mycelial biomass production, conducting a primary fermentation in said vessel to produce primarily mycelial biomasss essentially free of spores, transferring the mycelial biomass to at least one further vessel containing said primary fermentation medium and continuing the primary fermentation in said at least one further vessel while maintaining the culture in the exponential growth phase to produce primarily mycelial biomass essentially free of spores and

(c) transferring the mycelial biomass, from the primary fermentation to a final fermentation in a vessel containing a medium which contains no sporulation-suppressing component and has a high carbon:nitrogen ratio to thereby prevent further mycelial biomass production and conducting a final fermentation to optimize spore production with a yield of at least $2 \times 10^7$ spores/ml, separating said spores from the mycelial biomass, and concentrating said spores into a slurry, drying said spore slurry and adjusting the final moisture content of the dried spore product to between 12% and 33% moisture for storage.

2. A method according to claim 1 wherein the inoculum of *Colletotrichum gloeosporioides* f.sp. *malvae* consists of spores.

3. A method according to claim 1 wherein the inoculum of *Colletotrichum gloeosporioides* f.sp. *malvae* consists of mycelium.

4. A method according to claim 1 wherein the inoculum *Colletotrichum gloeosporioides* f.sp. *malvae* consists of spores and mycelium.

5. A method according to claim 1 wherein the primary fermentation medium contains an antibiotic component.

6. A method according to claim 1 wherein the volume of the primary fermentation is serially-expanded by transfer to a larger vessel or vessels.

7. A method according to claim 1 wherein the final fermentation medium includes the following components: sucrose (0–30 g/l), yeast extract (0–5 g/l), potassium phosphate (0–5 g/l), tryptic soy broth (0–30 g/l).

8. A method according to claim 7 wherein the final fermentation medium contains an antibiotic component.

9. A method according to claim 7 wherein the final fermentation medium has a pH in the range of 5.5–6.5, aeration in the range of 0.1–1.0 vvm, temperature in the range of 10–28° C., agitation in the range of 50–600 rpm, back pressure in the range of 0–0.5 bars and dissolved oxygen above 50%.

10. A method according to claim 1, wherein the spores produced during the final fermentation are separated from the mycelial biomass by a process selected from sedimentation, screening, sieving, straining, filtration or centrifugation.

11. A method according to claim 1 wherein the separated spores are concentrated into a slurry by a process selected from centrifugation or filtration.

12. A method according to claim 1 wherein the concentrated spore slurry is stabilized by the addition of a stabilizing component to the spore slurry.

13. A method according to claim 1 wherein the separated spores are dried by a process selected from tray-drying, freeze-drying or spray-drying.

* * * * *